(12) United States Patent
Redei et al.

(10) Patent No.: US 8,383,352 B2
(45) Date of Patent: Feb. 26, 2013

(54) DETECTION OF MATERNAL ALCOHOL EXPOSURE

(75) Inventors: Eva E. Redei, Chicago, IL (US); Pradeep K. Shukla, Chicago, IL (US); Laura J. Sittig, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 12/795,082

(22) Filed: Jun. 7, 2010

(65) Prior Publication Data

US 2010/0311067 A1 Dec. 9, 2010

Related U.S. Application Data

(60) Provisional application No. 61/184,374, filed on Jun. 5, 2009.

(51) Int. Cl.
*G01N 33/53* (2006.01)
(52) U.S. Cl. .................................... 435/7.1; 436/518
(58) Field of Classification Search .................. None
See application file for complete search history.

(56) References Cited

PUBLICATIONS

Tannahill et al. Clinical Endocrinology (2002) 56(6): 735-743.*
Iqbal et al. (J. Neuroendo. 2005 vol. 17, p. 600-608).*
Weinberg et al. (Alcoholsm Clinical and Experimental Research 1991 vol. 15, p. 711-716).*
Bearer et al. Alcohol Research & Health 2004 vol. 28, p. 38-43.*
Apostolidou et al. (2007) "Elevated placental expression of the imprinted PHLDA2 gene is associated with low birth weight," J Mol Med 85(4):379-87.
Barker et al (1993) "Fetal nutrition and cardiovascular disease in adult life," Lancet 341(8850):938-41.
Bianco AC and Kim BW (2006) "Deiodinases: implications of the local control of thyroid hormone action," J Clin Invest 116(10):2571-9.
Conigrave et al. (2003) "Traditional markers of excessive alcohol use," Addiction 98(Suppl2):31-43.
Geurts et al. (1981) "Alterations in circulating thyroid hormones and thyroxine binding globulin in chronic alcoholism," Clin Endocrinol (Oxf) 14(2):113-8.
Haycock & Ramsay, "Exposure of Mouse Embryos to Ethanol During Preimplantation Development: Effect on DNA Methylation in the H19 Imprinting Control Region," Biol Reprod. Epub Mar. 11, 2009.
Heinz et al (1996) "Long-lerm observation of the hypothalamic-pituitary-thyroid (HPT) axis in alcohol-dependent patients," Acta Psychiatrica Scandinavica 93(6):470-6.
Hernandez et al. (2002) "The Gene Locus Encoding Idothyronine Deiodinase Type 3 (Dio3) Is Imprinted in the Fetus and Expresses antisense Transcripts," Endocrinology. 143:4483-6.
Hernandez et al., (2006) "Type 3 deiodinase is critical for the maturation and function of the thyroid axis," J Clin Invest. 116:476-84.
Huang et al., (2002) "A 21-year-old woman with consumptive hypothyroidism due to a vascular tumor expressing type 3 iodothyronine deiodinase," J Clin Endocrinol Metab 87(10):4457-61.
Kilby et al., (1998) "Circulating thyroid hormone concentrations and placental thyroid hormone receptor expression in normal human pregnancy and pregnancy complicated by intrauterine growth restriction (IUGR)," J Clin Endocrinol Metab 83(8):2964-71.
Lin et al., (2007) "Differential regulation of imprinting in the murine embryo and placenta by the Dlk1-Dio3 imprinting control region," Development 134:417-26.
Mesquita et al., (2009) "Glucocorticoids and neuro- and behavioural development," Semin Fetal Neonatal Med 14 (3):130-5.
Morell et al., (1994) "Levels of L-T3 in maternal and foetal compartments following experimental modifications of the maternal thyroid state in rats," Arch Int Physiol Biochim Biophys 102(1):1-3.
Munck et al., (1990) "Glucocorticoid receptors and actions," Am Rev Respir Dis 141(2 Pt 2):S2-10.
Rodriguez-Garcia et al., (1995) "Effect of perinatal hypothyroidism on the developmental regulation of rat pituitary growth hormone and thyrotropin genes," Endocrinology 136(10):4339-50.
Schwitzgebel et al., (2009.) "Modeling intrauterine growth retardation in rodents: Impact on pancreas development and glucose homeostasis," Mol Cell Endocrinol 304(1-2):78-83.
Sharpe PC (2001) "Biochemical detection and monitoring of alcohol abuse and abstinence," Ann Clin Biochem 38(Pt 6):652-64.
Sibley et al., (2004) "Placental-specific insulin-like growth factor 2 (Igf2) regulates the diffusional exchange characteristics of the mouse placenta," Proc N atl Acad Sci USA 101(21):8204-8.
Sood et al., (2006) "Gene expression patterns in human placenta," Proc Natl Acad Sci USA 103(14):5478-83.
Tsai et al., (2002) "Genomic imprinting contributes to thyroid hormone metabolism in the mouse embryo," Curr Biol 12 (14):1221-6.
Weinberg et al., (2008) "Prenatal alcohol exposure: foetal programming, the hypothalamic-pituitary-adrenal axis and sex differences in outcome," J Neuroendocrinol 20(4):470-88.
Wilcoxon JS and Redei EE (2004) "Prenatal programming of adult thyroid function by alcohol and thyroid hormones," Am J Physiol Endocrinol Metab 287(2):E318-26.
Wilcoxon et al., (2005) "Behavioral deficits associated with fetal alcohol exposure are reversed by prenatal thyroid hormone treatment: a role for maternal thyroid hormone deficiency in FAE," Mol Psychiatry 10(10):961-71.
Yevtodiyenko et al., (2002) "Analysis of candidate imprinted genes linked to Klk1-Gtl2 using a congenic mouse line," Mamm Genome. 13:633-8.

* cited by examiner

*Primary Examiner* — Jacob Cheu
(74) *Attorney, Agent, or Firm* — Casimir Jones, S.C.

(57) ABSTRACT

The present invention provides methods, compositions, and systems for detecting in utero alcohol exposure by detecting expression level changes in certain biomarkers (e.g., in placental tissue). In certain embodiments, the biomarkers are selected from glucocorticoid receptor (GR), thyroid hormone receptor alpha (TRα), iodothyronine deiodinase III (Dio3) and G-protein α-subunit (Gsα).

23 Claims, 4 Drawing Sheets

US 8,383,352 B2

DETECTION OF MATERNAL ALCOHOL EXPOSURE

CROSS-REFERENCE TO RELATED APPLICATION

The present invention claims priority to U.S. Provisional Patent Application Ser. Nos. 61/184,374 filed Jun. 5, 2009, which is hereby incorporated by reference in its entirety.

STATEMENT REGARDING FEDERALLY SPONSORED RESEARCH OR DEVELOPMENT

This invention was made with government support under Grant No. AA017978 awarded by the National Institutes of Health. The government has certain rights in the invention.

FIELD OF THE INVENTION

The present invention relates to methods, compositions, and systems for detecting in utero alcohol exposure by detecting expression level changes in certain biomarkers (e.g., in placental tissue). In certain embodiments, the biomarkers are selected from glucocorticoid receptor (GR), thyroid hormone receptor alpha (TRα), iodothyronine deiodinase III (Dio3) and G-protein α-subunit (Gsα).

BACKGROUND

Current statistics indicate that one in 8 pregnant women consume alcohol (Floyd and Sidhu, 2004; herein incorporated by reference in its entirety). Fetal alcohol spectrum disorder (FASD) is a leading cause of non-genetic mental retardation and other neurodevelopmental deficits. FASD describes a continuum of permanent birth defects caused by maternal consumption of alcohol during pregnancy, which includes, but is not limited to fetal alcohol syndrome (FAS), partial fetal alcohol syndrome (PFAS), alcohol-related neurodevelopmental disorder (ARND), alcohol-related birth defects (ARBD), and fetal alcohol effect (FAE). The incidence of the FAS is between 1.3 and 4.6 per 1000 (Sampson et al., 1997; herein incorporated by reference in its entirety), while the prevalence of FAS and ARND combined is estimated to be as high as 9.1 per 1000 in the general population (Streissguth and O'Malley, 2000; herein incorporated by reference in its entirety). Each day, 6-22 infants are born with FAS in the US, but 87-103 more are born with ARND (Lupton et al., 2004; herein incorporated by reference in its entirety). The annual cost of FAS in the US is $3.6 billion, and there is no data regarding the cost of ARND.

A large body of data indicates that prenatal alcohol exposure can lead to deficits in overall cognitive ability, attention regulatory behaviors, adaptive responses and psychosocial adjustments in children and young adults (Mattson and Riley, 1998; Barr et al., 2006; Willford et al., 2006; herein incorporated by reference in their entireties). These deficits are observed in prenatal alcohol-exposed children with or without the diagnosis of FAS (Mattson and Riley, 2000; Barr et al., 2006; herein incorporated by reference in their entireties) and in the absence of mental retardation. The overall prevalence for attention deficit/hyperactivity (ADHD) and learning disorders together is close to 60% among youth diagnosed with fetal alcohol spectrum disorder (Bhatara et al., 2006; herein incorporated by reference in its entirety).

Fetal alcohol spectrum disorder (FASD) is a leading cause of non-genetic mental retardation and other neurodevelopmental deficits. Although alcohol biomarkers have been identified, most register alcohol exposure and not its toxicity per se. There is no accepted method for diagnosing prenatal ethanol exposure other than retrospective assessment of maternal drinking behavior.

SUMMARY OF THE INVENTION

The present invention provides methods, compositions, and systems for detecting in utero alcohol exposure by detecting expression level changes in certain biomarkers (e.g., in placental tissue). In certain embodiments, the biomarkers are selected from glucocorticoid receptor (GR), thyroid hormone receptor alpha (TRα), and iodothyronine deiodinase III (Dio3) and G-protein α-subunit (Gsα).

In some embodiments, the present invention provides biomarkers (e.g. GR, TRα, Dio3, Gsα) which exhibit altered expression levels (e.g. in placental, fetal, newborn, and/or offspring tissue). In some embodiments, the present invention provides biomarkers (e.g. GR, TRα, Dio3, Gsα) which exhibit altered expression levels (e.g. in placental, fetal, newborn, and/or offspring tissue) following in utero alcohol exposure when compared to average expression levels, control expression levels, and/or expression levels when not exposed to in utero alcohol. In some embodiments, the present invention provides methods comprising: detecting altered protein or mRNA expression of a biomarker gene in placental tissue, wherein the biomarker gene is selected from the group consisting of: glucocorticoid receptor (GR), thyroid hormone receptor alpha (TRα), iodothyronine deiodinase III (Dio3), and G-protein α-subunit (Gsα). In some embodiments, deviation of biomarker expression from control identifies in utero alcohol exposure. In some embodiments, the degree of deviation of biomarker expression from control characterizes the level of in utero alcohol exposure.

Accordingly, in some embodiments, the present invention provides a method for detecting prior in utero exposure in a subject, comprising providing a tissue sample; and detecting the expression of an in utero alcohol exposure biomarker (e.g., GR, TRα, Dio3, Gsα, etc.) in the sample. In some embodiments, the tissue sample comprises a placental tissue sample. In some embodiments, detecting expression comprises quantifying expression. In some embodiments, one or more proteins, peptides, or nucleic acid molecules (e.g., DNA, RNA) is detected or quantified. In some embodiments, a subject is a newborn, and the tissue sample comprises the subject's placenta. In some embodiments, detecting the expression of an in utero alcohol exposure biomarker (e.g., GR, TRα, Dio3, Gsα, etc.) comprises detecting the expression of one or more in utero alcohol exposure biomarkers (e.g. 1, 2, 3, 4, etc.). In some embodiments, detecting the expression of an in utero alcohol exposure biomarker (e.g., GR, TRα, Dio3, Gsα, etc.) comprises detecting the expression of a panel of in utero alcohol exposure biomarkers.

In some embodiments, detecting the expression of an in utero alcohol exposure biomarker (e.g., GR, TRα, Dio3, Gsα, etc.) comprises detecting the presence of biomarker (e.g., GR, TRα, Dio3, Gsα, etc.) mRNA. In some embodiments, detecting expression of an in utero alcohol exposure biomarker (e.g., GR, TRα, Dio3, Gsα, etc.) comprises exposing the biomarker mRNA to a nucleic acid probe complementary to the biomarker mRNA. In some embodiments, detecting expression of an in utero alcohol exposure biomarker (e.g., GR, TRα, Dio3, Gsα, etc.) comprises detecting the presence of a biomarker protein, polypeptide, or portion thereof. In some embodiments, detecting the presence of an in utero alcohol exposure biomarker (e.g., GR, TRα, Dio3, Gsα, etc.) polypeptide comprises exposing the biomarker polypeptide to an antibody specific to the biomarker polypeptide and detecting the binding of the antibody to the biomarker polypeptide. In some embodiments, the subject comprises a human subject.

The present invention also provides a method for selecting a therapeutic course of action, comprising providing a sample from a subject; detecting and/or quantifying the expression an in utero alcohol exposure biomarker (e.g., GR, TRα, Dio3, Gsα, etc.) in the sample; and treating the subject based upon the expression of the biomarker.

The present invention provides a kit for characterizing in utero alcohol exposure in a subject, comprising a reagent capable of specifically detecting the presence or absence of expression of an in utero alcohol exposure biomarker (e.g., GR, TRα, Dio3, Gsα, etc.); and, optionally, instructions for using the kit for characterizing in utero alcohol exposure in the subject. In some embodiments, the reagent comprises a nucleic acid probe. In some embodiments, the reagent comprises an antibody.

In particular embodiments, the biomarker gene is Dio3, and increased protein or mRNA expression is detected. In some embodiments, Dio3 expression is compared to expression of a control gene. In some embodiments, Dio3 expression is compared to average Dio3 expression in the absence of in utero alcohol exposure. In further embodiments, the altered Dio3 protein or Dio3 mRNA expression is as compared to a control gene (e.g., β-actin). In some embodiments, the ratio of Dio3 expression to β-actin expression is at least 1.3-fold higher (e.g. 2-fold higher) in samples from an in utero alcohol exposure subject (e.g. subject's placenta) than from a control subject.

In other embodiments, the biomarker gene is Gsα, and increased protein or mRNA expression is detected. In some embodiments, Gsα expression is compared to expression of a control gene. In some embodiments, Gsα expression is compared to average Gsα expression in the absence of in utero alcohol exposure. In further embodiments, the altered Gsα protein or Gsα mRNA expression is as compared to a control gene (e.g., β-actin). In some embodiments, the ratio of Gsα expression to β-actin expression is at least 1.3-fold higher (e.g. 2-fold higher) in samples from an in utero alcohol exposure subject (e.g. subject's placenta) than from a control subject.

In some embodiments, the biomarker gene is GR, and decreased protein or mRNA expression is detected (e.g., as compared to a control gene expression). In some embodiments, GR expression is compared to expression of a control gene. In some embodiments, GR expression is compared to average GR expression in the absence of in utero alcohol exposure. In further embodiments, the altered GR protein or GR mRNA expression is as compared to a control gene (e.g., β-actin). In some embodiments, the ratio of GR expression to β-actin expression is at least 1.5-fold reduced (e.g. 2-fold reduced) in samples from an in utero alcohol exposure subject (e.g. subject's placenta) than from a control subject.

In other embodiments, the biomarker gene is TRα, and decreased protein or mRNA expression is detected (e.g., as compared to a control gene expression). In some embodiments, TRα expression is compared to expression of a control gene. In some embodiments, TRα expression is compared to average TRα expression in the absence of in utero alcohol exposure. In further embodiments, the altered TRα protein or TRα mRNA expression is as compared to a control gene (e.g., β-actin). In some embodiments, the ratio of TRα expression to β-actin expression is at least 1.5-fold reduced (e.g. 2-fold reduced, 3-fold reduced) in samples from an in utero alcohol exposure subject (e.g. subject's placenta) than from a control subject.

In some embodiments, the methods further comprise diagnosing a subject associated with said placental tissue as exposed or likely exposed to maternal alcohol consumption when the subject was in utero. In particular embodiments, the present invention provides methods comprising: detecting Dio3 imprinting in brain tissue from a subject, where altered Dio3 imprinting indicates maternal alcohol consumption when the subject was in utero.

DETAILED DESCRIPTION

Figure 1:
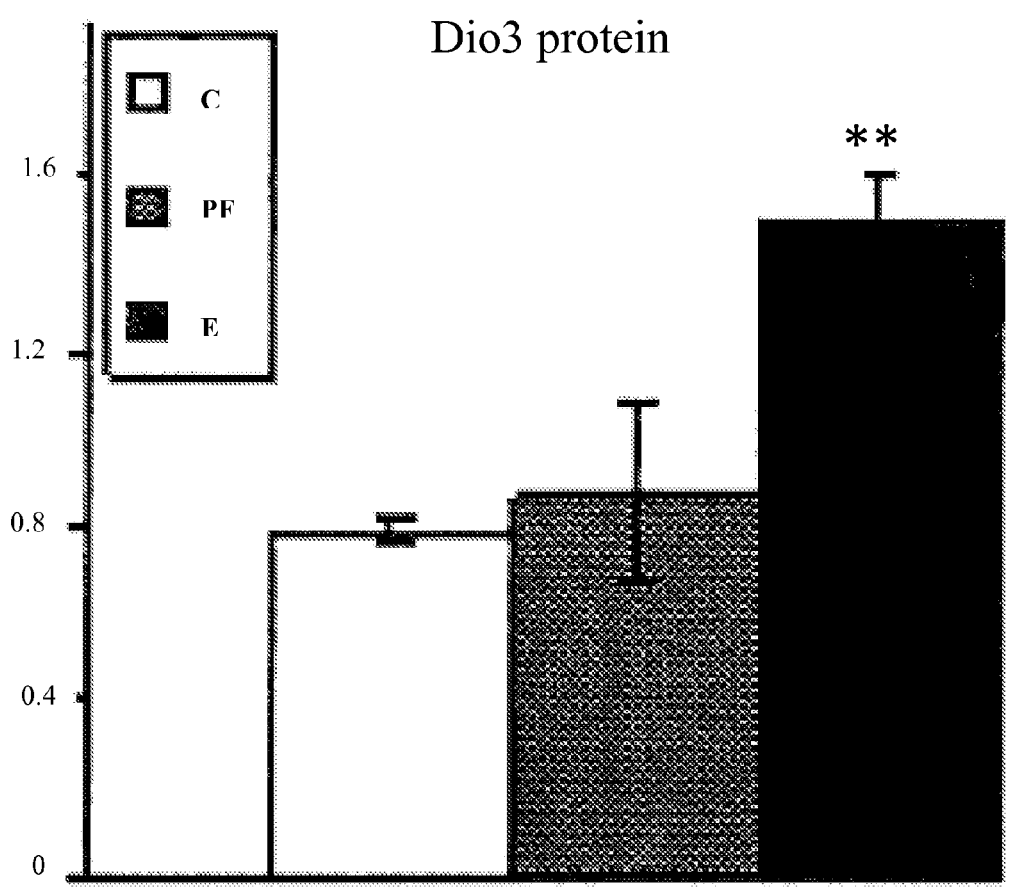
FIG. 1 shows up-regulation of Dio3 upon in utero exposure to ethanol, Dio3 protein levels in placenta were measured by Western blot analysis, and normalized to β-actin.

The present invention provides methods, compositions, and systems for detecting in utero alcohol exposure by detecting expression level changes in certain biomarkers (e.g., in placental tissue). In certain embodiments, the biomarkers are selected from glucocorticoid receptor (GR), thyroid hormone receptor alpha (TRα), iodothyronine deiodinase III (Dio3) and G-protein α-subunit (Gsα). In some embodiments, the present invention provides biomarkers (e.g. placental biomarkers) in an animal model of FASD that signal intrauterine alcohol exposure specifically. In some embodiments, biomarkers predict the degree of future alcohol-induced deficits. In some embodiments, the present invention provides biomarkers for the detection and/or characterization of FASD (e.g. FAS, PFAS, ARND, ARBD, and/or FAE). In some embodiments, the present invention provides discrimination between various syndromes and disorders on the fetal alcohol spectrum (e.g. FAS, PFAS, ARND, ARBD, and/or FAE). In some embodiments, the present invention provides detection and/or characterization of one or more syndromes and/or disorders on the fetal alcohol spectrum (e.g. FAS, PFAS, ARND, ARBD, and/or FAE).

In certain embodiments, the present invention provides methods for detecting teratogen exposure in utero. For example, work conducted during the development of the present invention identified four biomarkers for in utero alcohol exposure to be measured in the placenta: glucocorticoid receptor (GR), thyroid hormone receptor alpha (TRα), iodothyronine deiodinase III (Dio3) and G-protein α-subunit (Gsα). The expression changes of biomarkers (e.g. GR, TRα, Dio3, Gsα) are highly and consistently altered in the alcohol-exposed placenta compared to normal placenta over a substantial portion of the gestational period. In some embodiments, biomarkers (e.g. GR, TRα, Dio3, Gsα) are detected by any of the numerous detection methods provided in the art. In some embodiments, biomarkers (e.g. GR, TRα, Dio3, Gsα) provide a strategy for assessing the likelihood that ethanol-exposed offspring will experience other physiological and cognitive effects of FAE. In some embodiments, a subject with altered placental expression of biomarkers (e.g. GR, TRα, Dio3, Gsα) is likely (e.g. highly likely) to exhibit physiological and cognitive effects of a FASD. In some embodiments, recognition of the likelihood of physiological and cognitive effects of a FASD provides opportunity for the timely application of appropriate treatments to affected offspring according to the risk level accorded by this set of biomarkers. In some embodiments, the degree of altered expression correlates to the likelihood of physiological and cognitive effects of a FASD. In some embodiments, the degree of altered expression correlates to the severity of physiological and cognitive effects of a FASD.

In certain embodiments, the present invention provides methods comprising obtaining a placental sample (e.g., at delivery), isolating proteins (e.g., the biomarkers discussed above), and then determining the specific protein levels (e.g., by Western blotting). In other embodiments, mRNA levels of the biomarkers described above are determined. In some embodiments, the levels of proteins or mRNA are compared to controls (e.g., values obtained from a large number of placentas with no indication of maternal alcohol consumption).

Alcohol related neurodevelopmental disorder (ARND) results from maternal alcohol consumption during pregnancy yet ~12% of pregnant women consume alcohol. ARND presents as a cluster of learning, memory, social, and psychiatric impairments. Offspring exposed to alcohol in utero show similar neurodevelopmental deficits as offspring exposed to maternal hypothyroidism in utero, and both show thyroid dysfunction as adults. Alcohol-induced thyroid dysfunction in the mother decreases thyroid hormone availability to the fetus and thereby contributes to ARND (Wilcoxon et al. 2004; 2005; herein incorporated by reference in its entirety). Thyroid hormones in the fetal brain are largely derived from mother and transferred—via the placenta—to the fetus. Local activity of the iodothyronine deiodinase type-III (Dio3) enzyme, which inactivates triiodothyronine (T3) and thyroxine to the minimally active T2 and reverse T3 respectively, by inner ring deiodination, is the primary regulator of local T3 availability in the placenta and fetal brain.

Dio3 is an imprinted gene located within the 1-Mb Dlk1-Dio3 locus (human chromosome 16, mouse chr 14, homologous to rat chr 6). Reports indicate that Dio3 is expressed preferentially from the paternal allele in mouse embryonic tissues (Hernandez et al., 2002; Tsai et al., 2002; Yevtodiyenko, 2002; herein incorporated by reference in their entireties). Loss of imprinting at the Dlk1-Dio3 locus is lethal to the mouse embryo (Lin et al., 2007; herein incorporated by reference in its entirety) and a lack of Dio3 leads to embryonic thyrotoxinaemia and abnormal adult thyroid function (Hernandez et al., 2006; herein incorporated by reference in its entirety), indicating that increasing or decreasing the fetal dosage of Dio3 is detrimental to development. Alcohol has been shown to alter gene expression by altering epigenetic regulation (Haycock & Ramsay, 2009; herein incorporated by reference in its entirety). Therefore, while the present invention is not limited to any particular mechanism and an understanding of the mechanism is not necessary to practice the present invention, it is contemplated that maternal alcohol consumption interferes with the imprinting of Dio3 in the developing fetus, affecting Dio3 levels and contributing to the developmental consequences of ARND. Work conducted during the development of the present invention determined that ethanol alters Dio3 imprinting and total expression patterns in the fetal and adult frontal cortex and hippocampus with inversely affected thyroid hormone levels.

In some preferred embodiments, biomarkers (e.g., including but not limited to, those disclosed herein (e.g. GR, TRα, Dio3, Gsα) are detected by measuring the expression of corresponding mRNA in a sample. In some embodiments, mRNA expression is measured by any suitable method or combination of methods (e.g. hybridization, amplification, mass (e.g. mass spectrometry), sequencing, reverse transcription, etc.).

In other preferred embodiments, gene expression of biomarkers is detected by measuring the expression of the corresponding protein or polypeptide. Protein expression may be detected by any suitable method. In some embodiments, proteins are detected by immunohistochemistry or ELISA. In some embodiments, proteins are detected by their binding to an antibody raised against the protein.

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject. The present invention contemplates any method capable of receiving, processing, and transmitting the information to and from laboratories conducting the assays, information provides, medical personal, and subjects. For example, in some embodiments of the present invention, a sample (e.g., a semen, serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine or semen sample) and directly send it to a profiling center. Where the sample comprises previously determined biological information, the information may be directly sent to the profiling service by the subject (e.g., an information card containing the information may be scanned by a computer and the data transmitted to a computer of the profiling center using electronic communication systems). Once received by the profiling service, the sample is processed and a profile is produced (i.e., expression data) that is specific for the diagnostic or prognostic information desired for the subject. The profile data is then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor. In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers. In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition associated with the disease.

In other preferred embodiments, the present invention provides kits for the detection and characterization of maternal alcohol exposure. In some embodiments, the kits contain antibodies specific for one or more biomarkers (e.g. GR, TRα, Dio3, Gsα, etc.), in addition to detection reagents and buffers. In other embodiments, the kits contain reagents specific for the detection of mRNA or cDNA (e.g., oligonucleotide probes or primers). In preferred embodiments, the kits contain all of the components necessary, sufficient, or useful to perform a detection assay, including all controls, directions for performing assays, and any necessary software for analysis and presentation of results. In some embodiments, clinician or user supplies one or more components necessary, sufficient, or useful to perform a detection assay or specific to their desired use.

Experimental

The following is presented in order to provide certain exemplary embodiments of the present invention and are not intended to limit the scope thereof.

Example 1

Biomarkers for in Utero Ethanol Exposure

The following Example describes the findings in a rat animal model of FAE using alcohol exposure paradigm that has been used previously and that leads to consequences analogous to those in children exposed to ethanol in utero (Nelson 1986; Taylor 1988; Redei 1989; Halasz 1993; Redei 1993; Aird 1997; Revskoy 1997; Sinha 1997; Zafar 2000; Slone 2002; Wilcoxon 2003; Wilcoxon 2004; Wilcoxon 2005; herein incorporated by reference in their entireties). Alcohol-containing or isocaloric pair-fed liquid diet, or normal lab chow and water were administered to pregnant Sprague-Dawley (SD) dams during the last two weeks of gestation. Male and female offspring of alcohol (E), pair-fed (PF) or normal diet (C) consuming dams were tested.

Figure 2:
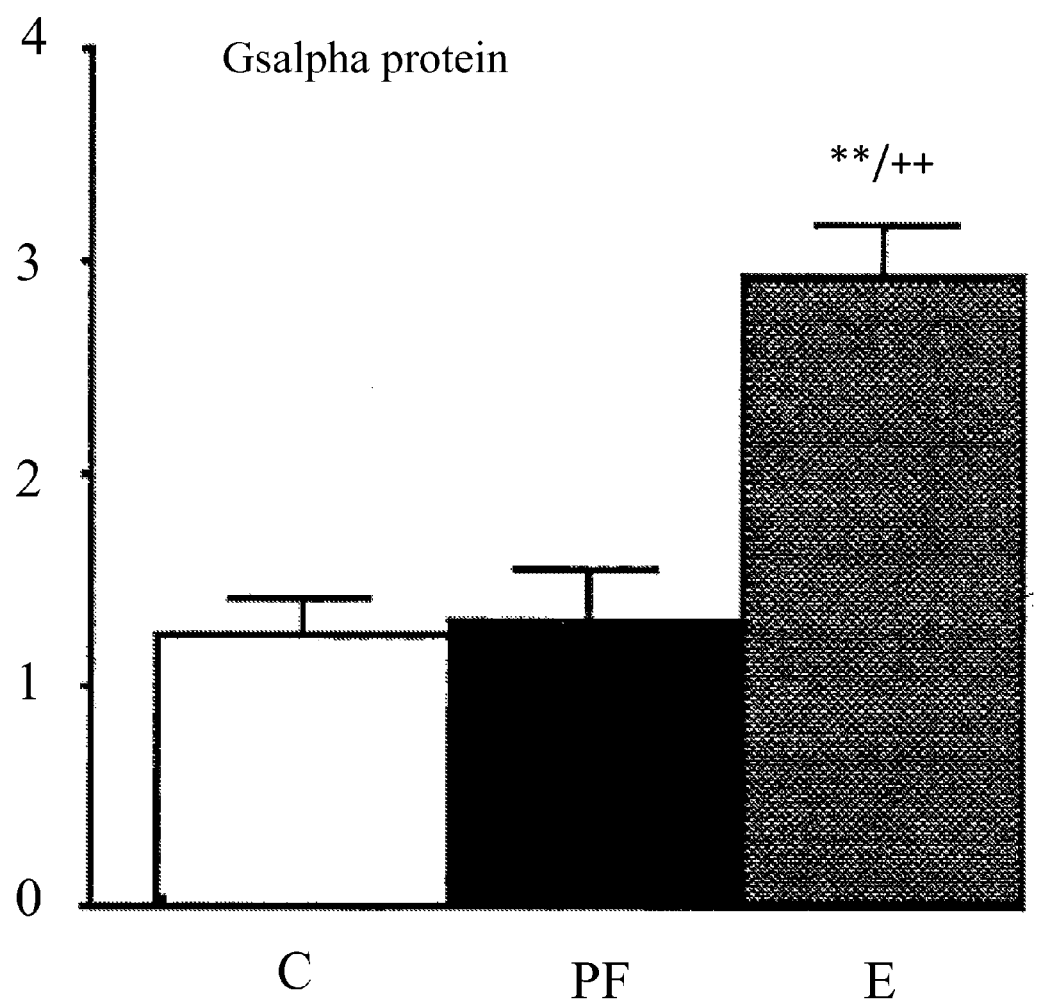
FIG. 2 shows up-regulation of Gsα upon in utero exposure to ethanol. Gsα protein levels in placenta were measured by Western blot analysis, and normalized to β-actin.
Figure 3:
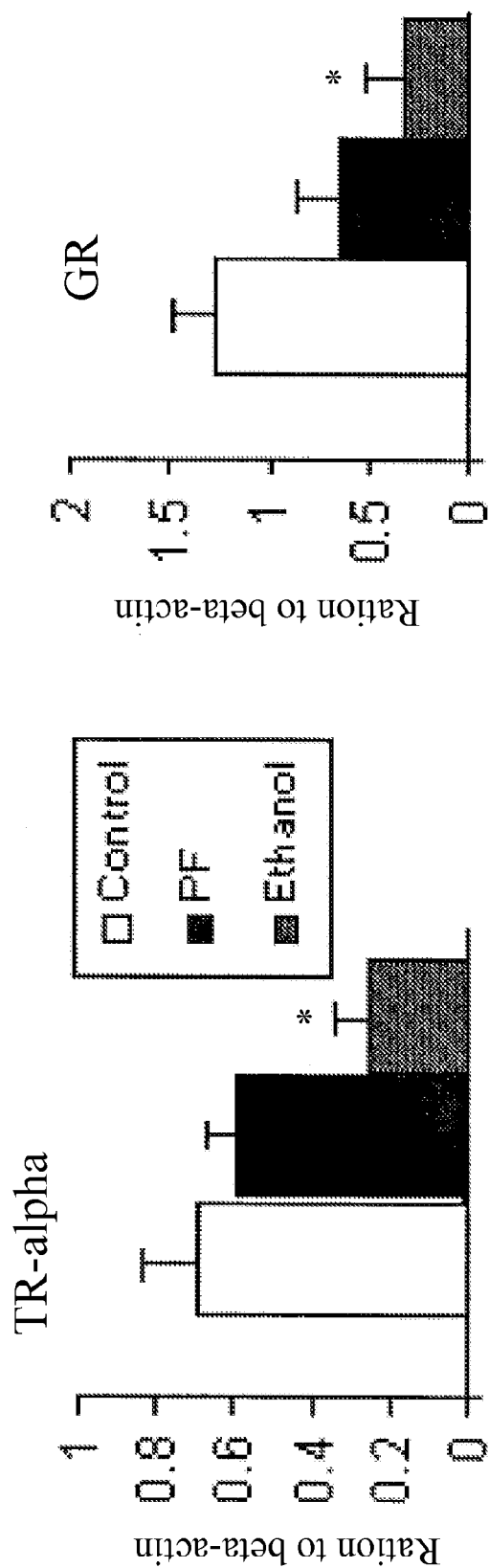
FIG. 3 shows down-regulation of TRα and GR upon in utero exposure to ethanol. Protein levels in placenta were measured by Western blot analysis, and normalized to β-actin.
Figure 4:
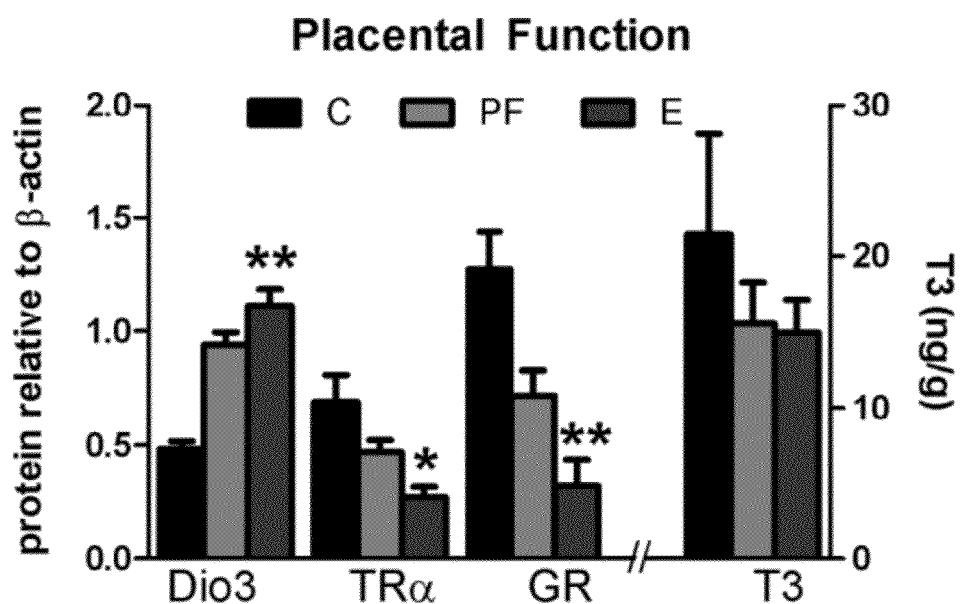
FIG. 4 shows placental expression levels of Dio3, TRα, GR, and T3 relative to the control gene β-actin under control, pair-fed, and ethanol conditions.

Upregulation of Dio3 and Gsα in FAE—Dio3 is the most important deiodinase during development, when levels of Dio3 are the highest in the placenta, and in the fetal brain. Gsα is the heterotrimeric G protein. Dio3 (SEE FIG. 1) and Gsα (SEE FIG. 2) are up-regulated upon in placental tissue that has undergone in utero exposure to ethanol. GR and TRα belong to the steroid/thyroid hormone receptor family of transcriptional regulators, and both are downregulated in the FAE placenta (SEE FIG. 3).

References

Hernandez et al., (2006). J Clin Invest. 116: 476-84.
Barker D J, Gluckman P D, Godfrey K M, Harding J E, Owens J A, Robinson J S (1993) Fetal nutrition and cardiovascular disease in adult life. Lancet 341(8850):938-41.
Benirschke K, Kaufmann P (2000) *Pathology a/the human placenta.* 4th ed. Springer, New York.
Bianco A C, Kim B W (2006) Deiodinases: implications of the local control of thyroid hormone action. J Clin Invest 116(10):2571-9.
Burd L, Roberts D, Olson M, Odendaal H (2007) Ethanol and the placenta: A review. J Matern Fetal Neonatal Med 20(5): 361-75.
Burton P J, Dharmarajan A M, Hisheh S, Waddell B J (1996) Induction of myometrial 11 beta hydroxysteroid dehydrogenase type 1 messenger ribonucleic acid and protein expression late in rat pregnancy. Endocrinology 137(12): 5700-6.
Conigrave K M, Davies P, Haber P, Whitfield J B (2003) Traditional markers of excessive alcohol use. Addiction 98 Suppl 2:31-43.
Del Boca F K, Darkes J (2003) The validity of self-reports of alcohol consumption: state of the science and challenges for research. Addiction 98 Suppl 2:1-12.
Floyd R L, Sidhu J S (2004) Monitoring prenatal alcohol exposure. Am J Med Genet 127C(1):3-9.
Geurts J, Demeester-Mirkine N, Glinoer D, Prigogine T, Fernandez-Deville M, Corvilain J (1981) Alterations in circulating thyroid hormones and thyroxine binding globulin in chronic alcoholism. Clin Endocrinol (Oxf) 14(2): 113-8.
Heinz A, Bauer M, Kuhn S, Kruger F, Graf K J, Rommelspacher H, Schmidt L G (1996) Long-lerm observation of the hypothalamic-pituitary-thyroid (HPT) axis in alcohol-dependent patients. Acta Psychiatrica Scandinavica 93(6): 470-6.
Henderson J, Gray R, Brocklehurst P (2007) Systematic review of effects of low-moderate prenatal alcohol exposure on pregnancy outcome. BJOG 114(3):243-52.
Huang S A, Fish S A, Dorfman D M, Salvatore D, Kozakewich H P, Mandel S J, Larsen P R (2002) A 21-year-old woman with consumptive hypothyroidism due to a vascular tumor expressing type 3 iodothyronine deiodinase. J Clin Endocrinol Metab 87(10):4457-61.
Kulaga V, Pragst F, Fulga N, Koren G (2009) Hair analysis of fatty acid ethyl esters in the detection of excessive drinking in the context of fetal alcohol spectrum disorders. Ther Drug Monit 31(2):261-6.
Liu C R, Li L Y, Shi F, Zang X Y, Liu Y M, Sun Y, Kan B H (2007) Effects of hyper- and hypothyroid on expression of thyroid hormone receptor mRNA in rat myocardium. J Endocrinol 195(3):429-38.
Mattson S N, Riley E P (1998) A review of the neurobehavioral deficits in children with fetal alcohol syndrome or prenatal exposure to alcohol. Alcohol Clin Exp Res 22(2): 279-94.
Mattson S N, Riley E P (2000) Parent ratings of behavior in children with heavy prenatal alcohol exposure and IQ-matched controls. Alcoholism: Clinical and Experimental Research 24(2):226-31.
Mesquita A R, Wegerich Y, Patchev A V, Oliveira M, Leao P, Sousa N, Almeida O F (2009) Glucocorticoids and neuro- and behavioural development. Semin Fetal Neonatal Med 14(3):130-5.
Morell M, Fernandez-Guillien F J, Lopez-Garcia J M (1994) Levels of L-T3 in maternal and foetal compartments following experimental modifications of the maternal thyroid state in rats Arch Int Physiol Biochim Biophys 102(1): 1-3.
Morini L, Marchei E, Vagnarelli F, Garcia Algar O, Groppi A, Mastrobattista L, Pichini S (2010) Ethyl glucuronide and ethyl sulfate in meconium and hair-potential biomarkers of intrauterine exposure to ethanol. Forensic Sci Int. Epub ahead of print.

Munck A, Mendel D B, Smith L I, Orti E (1990) Glucocorticoid receptors and actions. Am Rev Respir Dis 141(2 Pt 2):S2-10.

Paley B, O'Connor M J (2009) Intervention for individuals with fetal alcohol spectrum disorders: treatment approaches and case management. Dev Disabil Res Rev 15(3):258-67.

Pei J R, Rinaldi C M, Rasmussen C, Massey V, Massey D (2008) Memory patterns of acquisition and retention of verbal and nonverbal information in children with fetal alcohol spectrum disorders. Can J Clin Pharmacol 15(1): e44-56.

Rodriguez-Garcia M, Jolin T, Santos A, Perez-Castillo A (1995) Effect of perinatal hypothyroidism on the developmental regulation of rat pituitary growth hormone and thyrotropin genes. Endocrinology 136(10):4339-50.

Sampson P D, Streissguth A P, Bookstein F L, Little R E, Clarren S K, Dehaene P, Hanson J W, Graham J M, Jr. (1997) Incidence of fetal alcohol syndrome and prevalence of alcohol-related neurodevelopmental disorder. Teratology 56(5):317-26.

Sharpe P C (2001) Biochemical detection and monitoring of alcohol abuse and abstinence. Ann Clin Biochem 38(Pt 6):652-64.

Sinha P, Halasz I, Choi J F, McGivern R F, Redei E (1997) Maternal adrenalectomy eliminates a surge of plasma dehydroepiandrosterone in the mother and attenuates the prenatal testosterone surge in the male fetus. Endocrinology 138(11):4792-7.

Stewart S H, Law T L, Randall P K, Newman R (2009) Phosphatidylethanol and Alcohol Consumption in Reproductive Age Women. Alcohol Clin Exp Res.

Streissguth A P, O'Malley K (2000) Neuropsychiatric implications and long-term consequences of fetal alcohol spectrum disorders. Semin Clin Neuropsychiatry 5(3):177-90.

Weinberg J (1984) Nutritional issues in perinatal alcohol exposure. Neurobehav Toxicol Teratol 6(4):261-9.

Weinberg J, Sliwowska J H, Lan N, Hellemans K G (2008) Prenatal alcohol exposure: foetal programming, the hypothalamic-pituitary-adrenal axis and sex differences in outcome. J Neuroendocrinol 20(4):470-88.

Wilcoxon J S, Kuo A G, Disterhoft J F, Redei E E (2005) Behavioral deficits associated with fetal alcohol exposure are reversed by prenatal thyroid hormone treatment: a role for maternal thyroid hormone deficiency in FAE. Mol Psychiatry 10(10):961-71.

Wilcoxon J S, Nadolski G J, Samarut J, Chassande O, Redei E E (2007) Behavioral inhibition and impaired spatial learning and memory in hypothyroid mice lacking thyroid hormone receptor alpha. Behav Brain Res 177(1):109-16.

Wilcoxon J S, Redei EE (2004) Prenatal programming of adult thyroid function by alcohol and thyroid hormones. Am J Physiol Endocrinol Metab 287(2):E318-26.

Wilcoxon J S, Schwartz J, Aird P, Redei E E (2003) Sexually dimorphic effects of maternal alcohol intake and adrenalectomy on left ventricular hypertrophy in rat offspring. Am J Physiol Endocrinol Metab 285(1):E31-9.

Wojcik M H, Hawthorne J S (2007) Sensitivity of commercial ethyl glucuronide (ETG) testing in screening for alcohol abstinence. Alcohol Alcohol 42(4):317-20.

Wurst P M, Kelso E, Weinmann W, Pragst P, Yegles M, Sundstrom Poromaa I (2008) Measurement of direct ethanol metabolites suggests higher rate of alcohol use among pregnant women than found with the AUDJT—a pilot study in a population-based sample of Swedish women. Am J Obstet Gynecol 198(4):407 e1-5.

All publications and patents mentioned in the present application and/or listed above are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for detecting in utero alcohol exposure of a subject comprising:
   a) detecting test placenta expression levels of two or more biomarker genes, and test placenta expression level of a control gene, in test placental tissue, wherein said one or more biomarker genes are selected from the group consisting of: iodothyronine deiodinase III (Dio3), G-protein α-subunit (Gsα), glucocorticoid receptor (GR), and thyroid hormone receptor alpha (TRα),
   b) calculating at least one test placenta biomarker expression ratio by comparing at least one of said test placenta expression levels of said one or more biomarker genes to said test placenta expression level of said control gene,
   c) comparing said at least one test placenta biomarker expression ratio to at least one control placenta biomarker expression ratio, wherein said control placenta biomarker expression ratio is calculated from expression levels of said one or more biomarker genes and said control gene obtained from control placentas that have no indication of maternal alcohol consumption, and
   d) identifying said subject as exposed or likely exposed to maternal alcohol consumption in utero by detecting altered expression of said one or more biomarker genes in said test placental tissue, wherein said altered expression is selected from the group consisting of:
      i) wherein, for said Dio3, said test placenta biomarker expression ratio is at least 1.3 fold higher than said control placenta biomarker expression ratio,
      ii) wherein, for said Gsα, said test placenta biomarker expression ratio is at least 1.3 fold higher than said control placenta biomarker expression ratio,
      iii) wherein, for said GR, said test placenta biomarker expression ratio is at least 1.5 fold reduced compared to said control placenta biomarker expression ratio, and
      iv) wherein, for said TRα, said test placenta biomarker expression ratio is at least 1.5 fold reduced compared to said control placenta biomarker expression ratio.

2. The method of claim 1, further comprising providing a report to a clinician, wherein said report provides a diagnosis or risk assessment of maternal alcohol consumption when said subject was in utero based on said altered expression of said one or more biomarker genes.

3. The method of claim 1, further comprising treating said subject based upon said identifying said altered expression of said at least one or more biomarker genes.

4. The method of claim 1, wherein said detecting said test placenta expression levels of one or more biomarker genes comprises detecting biomarker mRNA.

5. The method of claim 1, wherein said detecting said test placenta expression levels of one or more biomarker genes comprises detecting biomarker protein, polypeptides, or fragments thereof.

6. The method of claim 1, wherein said biomarker gene is Dio3.

7. The method of claim 1, wherein said biomarker gene is Gsα.

8. The method of claim 1, wherein said biomarker gene is GR.

9. The method of claim 1, wherein said biomarker gene is TRα.

10. A method for detecting in utero alcohol exposure of a subject comprising:
    detecting altered expression of two or more biomarker genes in placental tissue compared to a control, wherein said altered expression of two or more biomarker genes is selected from the group consisting of at least two of the following: up-regulation of iodothyronine deiodinase III (Dio3), up-regulation of G-protein α-subunit (Gsα), down-regulation of glucocorticoid receptor (GR), and down-regulation of thyroid hormone receptor alpha (TRα).

11. The method of claim 10, wherein said at least two biomarker genes are Dio3 and TRα.

12. The method of claim 10, wherein said at least two biomarker genes are Gsα and Dio3.

13. The method of claim 10, wherein said at least two biomarker genes are GR and Dio3.

14. The method of claim 10, wherein said at least two biomarker genes are TRα and GR.

15. The method of claim 10, wherein said at least two biomarker genes are Gsα and GR.

16. The method of claim 10, wherein said at least two biomarker genes are Gsα and TRα.

17. A method for detecting in utero alcohol exposure of a subject comprising:
    a) detecting test placenta expression levels of two or more biomarker genes in test placental tissue, and
    b) comparing said test placenta expression levels to control placental levels for said two or more biomarker genes such that altered expression levels in said two or more biomarker genes for said test placentas are identified,
    wherein said altered expression of two or more biomarker genes is selected from the group consisting of at least two of the following: up-regulation of iodothyronine deiodinase III (Dio3), up-regulation of G-protein α-subunit (Gsα), down-regulation of glucocorticoid receptor (GR), and down-regulation of thyroid hormone receptor alpha (TRα), and
    wherein said control placenta levels comprise expression levels of said two or more biomarker genes from control placentas with no indication of maternal alcohol consumption.

18. The method of claim 17, wherein said at least two biomarker genes are Dio3 and TRα.

19. The method of claim 17, wherein said at least two biomarker genes are Gsα and Dio3.

20. The method of claim 17, wherein said at least two biomarker genes are GR and Dio3.

21. The method of claim 17, wherein said at least two biomarker genes are TRα and GR.

22. The method of claim 17, wherein said at least two biomarker genes are Gsα and GR.

23. The method of claim 17, wherein said at least two biomarker genes are Gsα and TRα.

* * * * *